United States Patent
Cheski et al.

(10) Patent No.: US 6,283,978 B1
(45) Date of Patent: Sep. 4, 2001

(54) METHOD AND APPARATUS FOR MICRODERMABRASION

(75) Inventors: Peter J. Cheski, 945 Kenfield Ave., Los Angeles, CA (US) 90049; Allen Weideman, Agoura Hills, CA (US)

(73) Assignee: Peter J. Cheski, Los Angeles, CA (US)

( * ) Notice: Subject to any disclaimer, the term of this patent is extended or adjusted under 35 U.S.C. 154(b) by 0 days.

(21) Appl. No.: 09/590,571

(22) Filed: Jun. 9, 2000

(51) Int. Cl.$^7$ .................................................. A61B 17/50
(52) U.S. Cl. .............................................................. 606/131
(58) Field of Search .................................... 606/131, 132, 606/159; 604/289, 290, 295, 296, 313, 315; 15/104.93, 104.94, 229.12, 229.13, 229.11, 229.14; 51/295, 296; 132/76.4, 317

(56) References Cited

U.S. PATENT DOCUMENTS

| | | |
|---|---|---|
| 110,162 | 12/1870 | Roorbach . |
| 243,671 | 6/1881 | Wilson . |
| D. 369,410 | 4/1996 | Holt ................... D24/147 |
| D. 369,658 | 5/1996 | Holt ................... D24/147 |
| 408,926 | 8/1889 | Palmer . |
| 448,409 | 3/1891 | Cassidy . |
| 454,956 | 6/1891 | Levy . |
| 528,317 | 10/1894 | Bailey . |
| 1,128,045 | 2/1915 | Reensteirna . |
| 1,214,556 | 2/1917 | Vene . |
| 1,255,819 | 2/1918 | Moffat . |
| 1,431,210 | 10/1922 | Blanchard . |
| 1,477,274 | 12/1923 | Mallory . |
| 1,586,411 | 5/1926 | Blom . |
| 1,597,589 | 8/1926 | Ferrari . |
| 1,851,811 | 3/1932 | Christie . |
| 1,963,389 | 6/1934 | Vardeman ............... 15/138 |
| 1,982,660 | 12/1934 | Handy ................... 15/157 |
| 2,091,807 | 8/1937 | Crum ..................... 51/205 |
| 2,156,494 | 5/1939 | Goodloe ................. 15/209 |
| 2,233,438 | 4/1941 | Troya ................... 123/76.4 |
| 2,233,811 | 3/1941 | Doty ..................... 123/269 |
| 2,341,354 | 2/1944 | Blood .................... 51/394 |
| 2,450,207 | 9/1948 | Silverman ............. 132/76.4 |
| 2,548,255 | 4/1951 | Cressler ................. 300/21 |
| 2,557,175 | 6/1951 | Cortes .................. 132/76.4 |
| 2,573,310 | 10/1951 | Collier .................. 132/76.4 |
| 2,616,436 | 11/1952 | Langley ................ 132/75.5 |
| 2,710,982 | 6/1955 | Gillem .................. 15/187 |
| 2,735,434 | 2/1956 | De Rossett ............ 132/76.4 |
| 2,736,917 | 3/1956 | Goldstein .............. 15/210 |
| 2,801,640 | 8/1957 | Steele .................. 132/75.4 |
| 2,921,585 | 1/1960 | Schuman ................ 128/355 |
| 2,966,691 | 1/1961 | Careron ................. 15/227 |
| 3,131,701 | 5/1964 | Emerson ............... 132/76.4 |
| 3,196,885 | 7/1965 | Emerson ............... 132/76.4 |
| 3,298,381 | 1/1967 | Adams .................. 132/76.4 |
| 3,299,505 | 1/1967 | Pionek ................... 30/29 |
| 3,318,318 | 5/1967 | Gewirz ................. 132/76.4 |

(List continued on next page.)

Primary Examiner—Pedro Philogene
(74) Attorney, Agent, or Firm—James Lawrence Sonntag

(57) ABSTRACT

In a method and apparatus for microdermabrasion, a free-flowing, abrasive particulate material is applied upon an application surface. The application surface has a non-abrasive, textured surface that provides holding cells in the surface, such that abrasive particulate material is non-adhesively held in the holding cells. The application surface is pressed or directed against a skin surface to be treated while applying a pressure and stroking the application surface along the skin surface. The pressure and the stroking is transmitted through the application surface in such a way that the particulate provides an abrasive action against the skin, during which time the particulate is held non-adhesively and free-flowing in the holding cells. After the tool is stroked over the skin several times, the particulate material and abraded skin particles are removed, preferably by brushing, from the surface.

11 Claims, 1 Drawing Sheet

U.S. PATENT DOCUMENTS

| | | | |
|---|---|---|---|
| 3,468,079 | 9/1969 | Kaufman | 51/378 |
| 3,491,396 | 1/1970 | Hesene | 15/118 |
| 3,611,468 | 10/1971 | Michael | 15/104.93 |
| 3,707,012 | 12/1972 | Lane | 15/104.93 |
| 3,985,521 | 10/1976 | Borchard et al. | 51/295 |
| 4,111,666 | 9/1978 | Kalbow | 51/295 |
| 4,286,610 | 9/1981 | Jones et al. | 132/76.4 |
| 4,381,792 | 5/1983 | Bush, Jr. et al. | 132/75.6 |
| 4,459,987 | 7/1984 | Panghorn | 128/355 |
| 4,541,443 | 9/1985 | Brothers et al. | 132/75.6 |
| 4,572,187 | 2/1986 | Schetrumpf | 128/355 |
| 4,611,361 | 9/1986 | Shinkai | 15/104.93 |
| 4,613,446 | 9/1986 | Magyar | 252/91 |
| 4,712,552 | 12/1987 | Panghorn | 128/355 |
| 4,817,651 | 4/1989 | Crisp et al. | 134/102 |
| 4,992,476 | 2/1991 | Geria | 514/782 |
| 4,998,984 | 3/1991 | McClendon | 206/205 |
| 5,015,266 | 5/1991 | Yamanoto | 51/293 |
| 5,037,432 | 8/1991 | Molinari | 606/131 |
| 5,100,412 | 3/1992 | Rosso | 606/131 |
| 5,176,155 | 1/1993 | Rudolph, Jr. | 132/76.4 |
| 5,800,446 | 9/1998 | Banuchi | 606/131 |
| 5,816,266 * | 10/1998 | Cone | 132/76.4 |
| 5,954,730 | 9/1999 | Bernabei | 606/131 |
| 5,997,549 | 12/1999 | Sauceda et al. | 606/131 |
| 6,017,351 | 1/2000 | Street | 606/131 |
| 6,027,402 * | 2/2000 | Oliver | 132/76.4 |
| 6,142,155 * | 11/2000 | Rudolph | 132/76.4 |

* cited by examiner

METHOD AND APPARATUS FOR MICRODERMABRASION

FIELD OF THE INVENTION

This invention relates to a method and apparatus for microdermabrasion, particularly for cosmetic and/or therapeutic treatment of human tissue.

BACKGROUND OF THE INVENTION

Currently the most commonly used systems for producing microdermabrasion are air entrainment systems that involve a vacuum or pressure apparatus that directs a flow of air carrying a reducing substance in the form of a particulate abrasive substance against the portion of the skin being treated. While these systems have been shown to be safe and effective, they suffer from disadvantages. In particular, the systems are mechanically complex and expensive. The treatment is usually conducted in a medical facility and applied by trained personnel or a physician. Accordingly, for the patient the treatments are both inconvenient and costly. Examples of these systems are disclosed in U.S. Pat. Nos. 5,037,432, 5,100,412, and 5,954,730.

It would be an advance in the art to provide a microdermabrasion system that is as safe and effective as air entrainment systems currently used, but are less complex, less expensive, and adaptable for use by the patient in his home.

Abrasive pads, files, and the like, are known in the art, which comprise an abrasive surface that is rubbed over the skin surface to abrade the skin. The abrasive surface may include ridges, sharp edges, blades or projection that function to abrade and scrape the skin surface. The abrasive surface also may include abrasive substances imbedded in the surface, or adhered to and/or protruding from the surface. These devises have been used to remove corns and calluses, and the like, but are not commonly used for microdermabrasion applications. A problem with these abrasive-surface devices is that it is difficult prevent overuse and excessive abrasion of the skin. As the surface is stroked over the skin, there is very little indication when the abrasion becomes excessive and begins to damage the skin. This is particularly a problem with inexperienced or untrained persons who in their zeal to see improvement are apt to over-abrade and damage the skin.

OBJECTS OF THE INVENTION

It is, therefore, an object of the invention to provide a microdermabrasion system that is safe and effective, but without the disadvantages of prior-art systems.

Another object of the invention is to provide a microdermabrasion system that is not mechanically complex and inexpensive to use.

Another object of the invention is to provide a microdermabrasion system that can be used by the patient at his own convenience in his home.

Another object of the invention is to provide a microdermabrasion system that is simpler to use than prior-art systems and does not require extensive training or expertise to use.

Further objects of the invention will become evident in the description below.

BRIEF SUMMARY OF THE INVENTION

The present invention is involves a method and apparatus for removing surface portions of human tissue in a controlled and safe manner. The method of the invention is particularly useful for the treatment of scars, stretch marks, acne, facial pigmentation, wrinkles, skin aging, sun damage and exposure, crows feet and other skin conditions, on the face, neck, arms and hands.

The method of the present invention is not mechanically complex, so that it does not require highly trained personnel to treat the patient and it can be used in self-treatment by the patient. With proper instruction, the patient may safely practice the method at her home at her own convenience.

The present method has been shown to be at least as effective as air entrainment systems currently in use. In addition, it has been found that the collagen and elastin in the dermis of the skin are stimulated and remodeled by the present method. Accordingly, the tone and elasticity of the skin are improved.

The present method also enhances the mechanisms, action and depth of penetration of other skin treatments. The aged, scarred, or damaged surface of the epidermis is removed, exposing younger and healthier cells, and increasing the permeability of the epidermis. Accordingly, if the microdermabrasion method of the present invention is soon followed by treatment with appropriate creams, and the like, the action of these treatments is enhanced. Such treatments may include treatment with collagen elastin creams, hydration creams, and sun blocking agents. Post treatments may also include skin-messaging techniques that further stimulate and remodel the elastin.

In summary, the present method comprises applying an abrasive particulate material to an application surface. The application surface is textured to carry or hold the particulate in a non-adhering or non-adhesive manner. The particulate is held in holding regions, cells or chambers that are provided by the surface texture. For example, the holding regions or cells may be provided in the surface texture by grooves, pits, indentations or the like that hold the particulate material and maintain the particulate material at the skin surface during the microdermabrasion process.

In the microdermabrasion process of the present invention, the particulate is applied to the application surface and the application surface moved along the skin with some pressure against the skin. Particulate does not generally adhering to the skin and the application surface. Therefore, it remains free flowing in the cells, and will tend to flow and circulate, and move in the cell and mix with abraded skin particles within the cells. The structure of the cells is such that they hold and retain the particulate in this flowing state in the cell during the micro-abrasion process. The movement and circulation of the particulate in the cells and the pressure against the skin provide cutting action that micro-abrades the skin surface. Thus, the abrasion is provided by the loose and flowing the particulate, and not by an abrasive action from a fixed abrasive surface. After a time particulate will be lost from the cells, and the abrasive action will diminish. This provides a safety against over-abrasion in the event the stroking action is continued too long. Unlike abrasive surfaces, the abrasive action of the present invention will gradually diminish, minimizing the possibility that excessive stroking will over abrade and damage the skin.

The application surface functions to transmit pressure and provide movement required for abrasion by the particulate. It also functions to apply the particulate to the skin surface and hold the particulate adjacent to the skin in a non-adhesive or non-sticking manner while the particulate provides the cutting an abrading action to the skin surface. Accordingly, the texture of the application surface should be designed such that there is no abrasive or cutting action from the surface itself, so that essentially all of the abrasion is essentially from the particulate material.

In an alternate embodiment of the invention, the particulate material is mixed with a cream or other like substance. In this embodiment, the holding cells carry the cream and the particulate, and as described above the abrasion is provided by the particulate mixed in the cream, as the cream and particulate circulates in the holding cells. The cream may provide some holding action for the particulate, but the abrasive action occurs when the cream/particulate is allowed to flow.

The application surface may be of a rigid material, such as mold plastic, or may be flexible (as a cloth) for situations where the greater conformance to the skin is required, such for wrinkles. The holding cells for the particulate may be provided by any suitable construction, such as by grooves perpendicular to the direction of movement of the tool. Any other constructions that provide the holding action and are non-abrasive are suitable, such as, for example, pits, tread patterns, weave patterns, crooked or straight grooves or ridges, or any combination of these. The apparatus of the invention is constructed so that an even pressure and movement can be applied by the application surface onto the skin. A preferred construction allows pressure to be applied by the palm of the hand, rather than through the fingers. Such a construction is illustrated in the specific embodiment illustrated below.

DETAILED DESCRIPTION OF THE INVENTION

Suitable particulate materials include any fine, abrasive materials, such as those used in the prior-art air entrainment systems, which usually are corundum (alumina) powders. The particulate material should not tend to cake or compact so as to prevent flow in the holding cells of the application surface. Accordingly, free flowing particulate materials are preferred, but other materials that provide the abrasive action described herein are suitable. Other suitable powdered materials that may be used or those that are non-toxic, non-caking and function to provide the desire abrasive action, with the correct particle size to be carried in the holding cells or grooves of the application surface. Suitable materials include, but are not limited to, fine particulate crystalline substances (e.g., sodium chloride crystals), particulate ceramics, particulate metals, diamond particles, hard organic abrasives, or other particulate materials used for cleaning or abrasion of surfaces.

Figure 1:
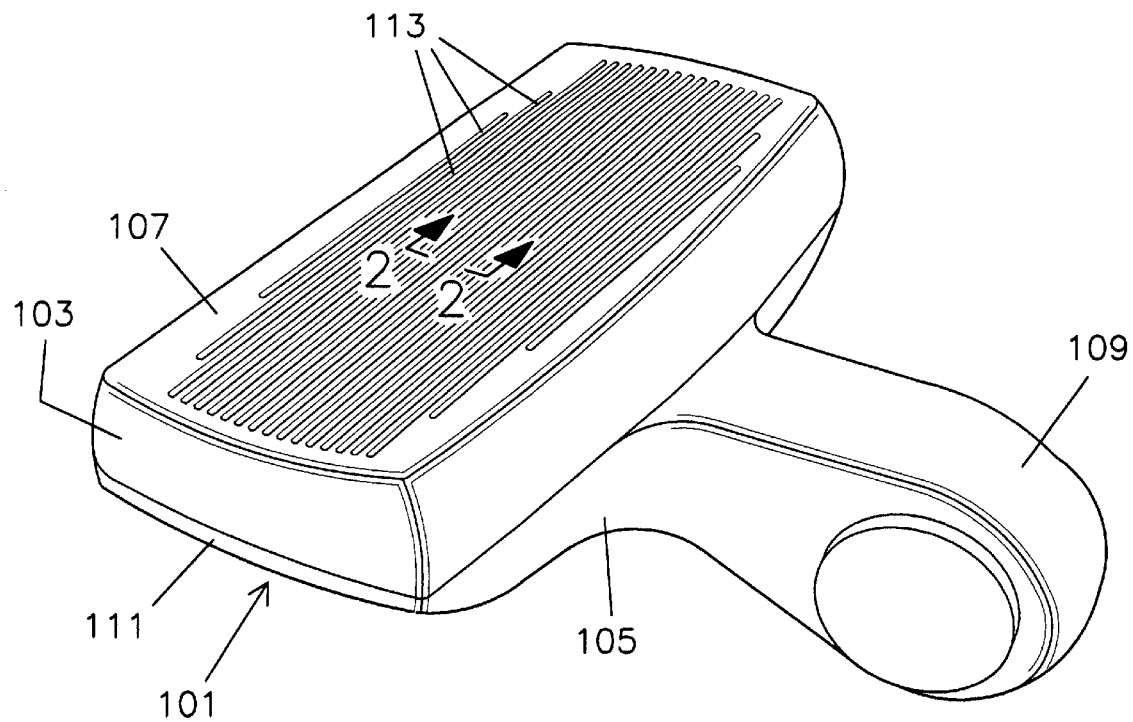
FIG. 1 is a perspective view of a microdermabrasion tool of the invention.

Referring to FIG. 1, a microdermabrasion tool 101 of the invention comprises a front and rear housing 103, 105 of molded ABS plastic. The front housing 103 includes the application surface 107 of the tool. The rear housing 103 is molded with a fulcrum handle 109, which during use of the tool, rests in the palm of the user. The surface 111 of the rear housing 105 opposite the fulcrum handle is dimensioned and shaped to allow the middle fingers of the hand to press down on the housing, using leverage, with the fulcrum handle in the palm as a fulcrum, to apply pressure on the skin as the application surface is stroked across the skin.

On the front housing 103 the application surface 107 is textured with grooves 113 molded into the surface to create the small hollows or holding cavities that non-adhesively hold the particulate material during microdermabrasion. The grooves 113 are generally disposes perpendicular to or across in a nonparallel direction to the direction in which the tool is stroked across the skin. This is to promote the retention of the particulate in the grooves.

Figure 2:
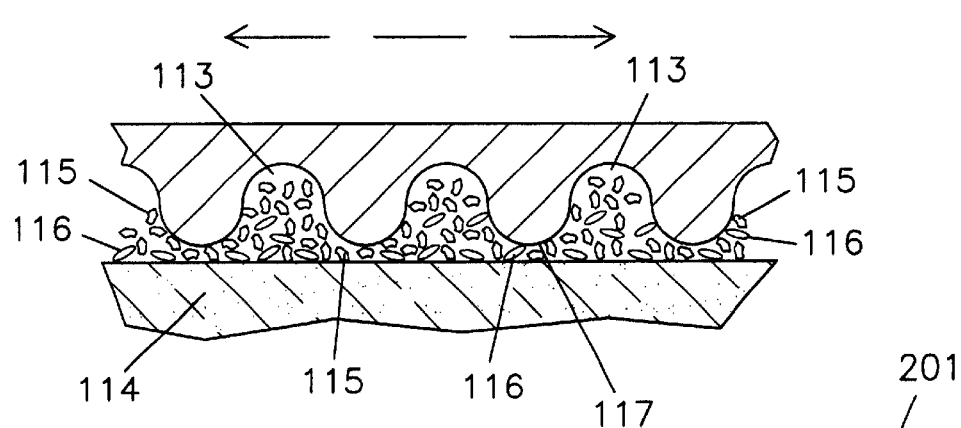
FIG. 2 is a cross-section of the grooved application surface of the tool of FIG. 1 through line 2—2.

Reference is now made to FIG. 2, which shows a cross-section of the grooves 113 in the application surface 107 holding the particulate material 115. In the practice of the invention, the particulate material is applied in the grooves 113, and the application surface 107 is stroked across the skin 114 (see arrows). As the application surface is stroked over skin, the stroking motion induces a circulating flow or movement in the particulate 115, which provides a cutting action against the skin and moves abraded skin 116 from the surface. The stroking also pulls against the grooves, which traps particulate between the skin and high points 117 between the grooves, which also provides an abrasive action against the skin.

The configuration, depth and width of the holding cells are not highly critical but are selected to provide the non-adhesive holding and mixing flow of the abrasive, as described herein. In the configuration of FIG. 1, grooves with a width of 0.030 inches and depth of 0.03 inches have been found suitable. The holding cells are structured, such that without particulate, they provide no abrasive action to the skin, since the abrasive action is provided by the particulate. Accordingly, sharp or pointed edges, serrated surfaces, and the like that would cut or abrade the skin are undesirable. The smooth and rounded profile illustrated in FIG. 2 has been found suitable.

Referring again to FIG. 2, during the stroking of the skin, the particulate material 115 is gradually lost from the grooves 113. If the stroking is continued for an extended time, much of the particulate material will be lost, leaving the non-abrasive application surface 107 against the skin. Thus, over-abrasion of the skin is essentially prevented, as the abrasive action of the tool is gradually lost during the stroking of the tool.

Figure 3:
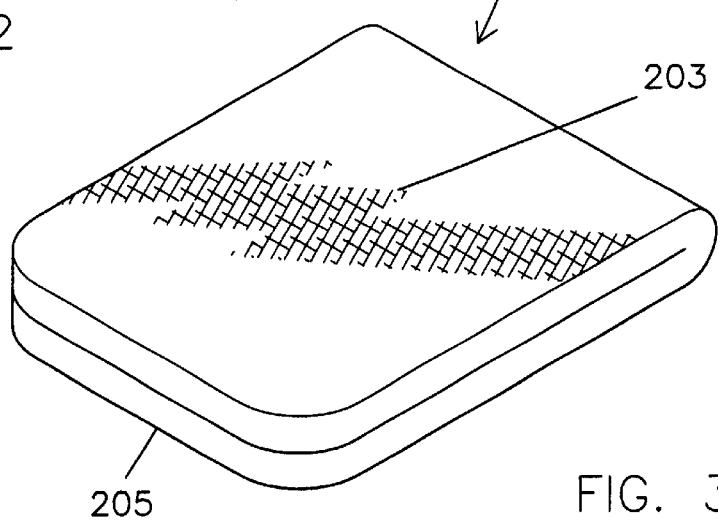
FIG. 3 is a perspective view of flexible microdermabrasion tool of the invention.

Reference is made to FIG. 3, which is a microdermabrasion tool of the invention formed as pad. The pad 201 has an application surface 203 of a tightly woven cloth that has a surface that provides the holding cavities for the particulate. It is used by applying pressure on the back of the pad 205 and stroking the application surface containing the particulate over the skin. This embodiment of the invention is particularly adapted for microdermabrasion of wrinkles and irregular surfaces around the nose and eyes.

As an illustration of the method of the invention, the skin area to be cleansed is cleansed, using, for example, a cleansing pad. The skin should be dry, so that the particulate does not adhere or cake to the skin or the tool.

A small amount of the particulate, about, about the amount as big as your finger tip on an applicator surface of an abrasion tool, such as one illustrated in FIG. 1. A cream may be added, preferably in an equal amount, if the skin is dry or irritated.

The crystals are applied to the skin by pressing the application surface against the skin and with a gentle pressure the tool is stroked 10 to 20 times perpendicular to the grooves with gentle pressure. Using the tool in FIG. 1, this routine is applied to the cheeks, jaws, forehead and neck.

For wrinkles, crows-feet, and the region around the nose and eyes, a conforming applicator tool, such as that illustrated in FIG. 3 is used. In like manner the particulate is applied to the applicator surface and used to micro-abrade by applying gentle pressure and stroking the tool.

After the treatment, a brush may be used to remove loose particulate and abraded skin particles. The skin may now be optimally treated with other skin treatments, such as collagen and elastin cream, hydrating cream, and/or sun block creams.

While this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention.

What is claimed is:

1. A method for microdermabrasion comprising;

applying an abrasive particulate material upon an application surface, the application surface having a non-abrasive, textured surface that provides holding cells in the surface, such that the abrasive particulate material is non-adhesively held in the holding cells, directing the application surface against a skin surface to be treated while applying a pressure and stroking the application surface along the skin surface, the pressure and the stroking being transmitted through the application surface such that the particulate material circulates in the holding cells to provide an abrasive action against the skin.

2. A method as in claim 1 wherein the holding cells are provided by grooves in the surface that are not parallel to the direction the application surface is being stroked.

3. A method as in claim 1 wherein the holding cells are provided by grooves in the surface that are essentially perpendicular to the direction the application surface is being stroked.

4. A method as in claim 1 wherein the pressure is applied by directing pressure from a palm of a hand on structure associated with the application surface.

5. A method as in claim 1 wherein the pressure is applied by directing pressure from fingers of a hand on structure associated with the application surface.

6. A method as in claim 1 wherein the particulate material is mixed with a cream.

7. A tool for microdermabrasion comprising;

an application surface with a textured non-abrasive surface that provides holding cells for non-adhesively holding an abrasive particulate material, structure associated with the application surface for transmitting a pressure and motion to the application surface when it is applied to a skin surface.

8. A tool as in claim 7 wherein the holding cells are provided by grooves in the application surface that are not parallel to the direction the application surface is being stroked.

9. A tool as in claim 7 wherein the holding cells are provided by grooves in the application surface that are essentially perpendicular to the direction the application surface is being stroked.

10. A tool as in claim 7 wherein the structure associated with the application surface is structured to directing pressure from a palm of a hand.

11. A tool as in claim 7 wherein the structure associated with the application surface is structured to directing pressure from fingers of a hand.

\* \* \* \* \*